United States Patent [19]

Rabson et al.

[11] Patent Number: 5,837,512

[45] Date of Patent: Nov. 17, 1998

[54] HIV-1 VECTORS

[75] Inventors: Arnold B. Rabson, Princeton; Hsin-Ching Lin, Edison, both of N.J.; Marion Bodkin, Massapequa, N.Y.; Roger Strair, Skillman, N.J.

[73] Assignee: University of Medicine & Dentistry of NJ, Newark, N.J.

[21] Appl. No.: 574,586

[22] Filed: Dec. 14, 1995

Related U.S. Application Data

[63] Continuation-in-part of Ser. No. 247,788, May 23, 1994, abandoned.
[51] Int. Cl.[6] .............................. C12N 15/86; C12N 5/10; C12N 15/64; C12N 15/49
[52] U.S. Cl. .................. 435/172.3; 424/93.2; 435/320.1
[58] Field of Search .............................. 435/320.1, 172.3; 424/93.2

[56] References Cited

PUBLICATIONS

"Report and Recommendations of the Panel to Assess the NIH Investment in Research on Gene Therapy," Orkin and Motulsky, Co–chairs, Dec. 7, 1995.

Sutton, The Lancet 337:1553 (1991).

Johnston et al., Science 260:1286–1293 (1993).

Lu et al., Journal of Virology 63(9):4115–4119 (1989).

Marshall Science 269:1050–1055 (1995).

*Primary Examiner*—Johnny F. Railey, II
*Attorney, Agent, or Firm*—Richard R. Muccino

[57] ABSTRACT

The present invention pertains to a genetically altered human immunodeficiency virus type 1 (HIV-1) which replicates only in human CD4+ cells that express the Tax protein of Human T-cell Lymphotropic Virus Type I (HTLV-I), wherein the HIV long terminal repeat (LTR) promoter and enhancer sequences (NF-kappa-B and Sp1 binding sites) of the genetically altered human immunodeficiency virus type 1 have been replaced by two copies of the HTLV-I LTR 21 base pair repeat Tax-responsive element (TRE). The present invention also pertains to methods for killing HTLV-1 infected cells in humans with HTLV-1 disease (HTLV-1 tumors and HAM/TSP) with the novel genetically altered human immunodeficiency virus type 1 (HIV-1).

3 Claims, 7 Drawing Sheets

Tax-Expressing Cell Lines

Tax-Minus Cell Lines

HIV-1 VECTORS

This is a continuation-in-part application of patent application Ser. No. 08/247,788, filed 23 May 1994, now abandoned.

BACKGROUND OF THE INVENTION

FIELD OF THE INVENTION

This invention relates to genetically engineered human cytopathic viruses which are altered by recombinant DNA techniques to specifically replicate in human tumor cells. Specifically, the human immunodeficiency virus type 1 (HIV-1) was genetically altered such that it will only replicate in human CD4+ cells that express the Tax protein of the Human T-cell Lymphotropic Virus Type I (HTLV-I). This genetic alteration was accomplished by replacement of the HIV long terminal repeat (LTR) promoter and enhancer sequences (NF-kappa-B and Sp1 binding sites) by two copies of the HTLV-I LTR 21 base pair repeat Tax-responsive element (TRE). Introduction of the TREs into the HIV-1 LTR results in production of an HIV that replicates in, and is cytotoxic for, HTLV-1-infected cells (expressing the HTLV-I Tax protein) but does not efficiently replicate in CD4+ cells lacking HTLV-I Tax, such as normal human peripheral blood mononuclear cells. This invention also relates to methods for preparing and using the genetically engineered human cytopathic viruses.

DESCRIPTION OF THE BACKGROUND

The human immunodeficiency virus type 1(HIV-1) is a cytopathic retrovirus that is the cause of the acquired immune deficiency syndrome (AIDS). The ability of HIV to replicate in, and to kill, human CD4+ T cells is dependent on efficient expression of HIV genes. Efficient expression of HIV RNA is mediated through cis-acting sequences that form the HIV enhancer and promoter in the HIV long terminal repeat (LTR) (see FIGS. 1A and 1B). Viral gene expression is controlled by both the interactions of the virally-encoded Tat protein with the TAR region of newly synthesized HIV RNA, and by interactions of normal cellular transcription factors with their cognate binding sites in the HIV LTR DNA (reviewed in Antoni, B. A. et al. 1994, Advances in Virus Res., 43: 53–145). Of particular importance in supporting HIV RNA transcription are the interactions of the cellular transcription factors Sp1 and NF-kappa-B with the LTR. Simultaneous deletion of the binding sites for these factors results in the loss of HIV replicative ability (Leonard et al., 1989, J. Virol. 63: 4919–4924, 1989). Alterations of either the Sp1 or NF-kappa-B binding sites result in variable effects on HIV replication in different cell types. The relative requirements for these binding sites for different transcription factors varies in different cell types depending on the levels of transcription factors present in the different cells. For example, deletion of the Sp1 binding sites results in loss of HIV replication in some T cells, but not in others (Parrott et al., 1991, J. Virol. 65: 1414–1419, 1991). In the absence of Sp1 binding, HIV replication becomes critically dependent on interactions of cellular transcription factors with other binding sites remaining in the LTR. The cell lines that support replication of HIV deleted in the LTR Sp1 binding sites contain high levels of nuclear NF-kappa-B which can compensate for the loss of Sp1 binding. Conversely, cells which contain only low levels of NF-kappa-B binding activity fail to support replication of HIV deleted in the Sp1 binding sites. Thus, alterations of the nature of cellular transcription factor binding sites present in the HIV LTR can affect the range of cell types susceptible to HIV replication. A further demonstration of this was seen in data indicating that the host range of HIV varies following substitution of the enhancer elements of other viruses such as murine leukemia virus or the human cytomegalovirus immediate early gene into the HIV LTR (Chang et al., 1993, J. Virol. 67: 74314 752).

HTLV-1 was the first human retrovirus to be identified (Poiesz et al., 1980, Proc. Natl. Acad. Sci. U.S.A., 77: 7415–7419). HTLV-1 infection is endemic in a number of parts of the world including Africa, the Mediterranean basin, the Caribbean and southeastern U.S., and islands in the southern part of Japan. HTLV-1 infection is associated with two different human diseases. One is a neurological disorder referred to as tropical spastic paraparesis (TSP) or HTLV-associated myelopathy (HAM) (reviewed in *McFarlin, D. E. and Koprowski, H,* 1990, Curr. Topics Microbiol. Immunol.160: 100–119). This disorder develops in 3—4% of HTLV-1 infected individuals. The pathogenic mechanisms that result in TSP/HAM are unknown, however, HTLV-1 infection of CD4+ T cells is an integral part of the disease process. HTLV-1 infection is also associated with the development of a subset of lymphomas and leukemias of CD4+ T cells referred to as adult T-cell leukemia/lymphoma (ATL) (reviewed in Ambinder, R. F., 1990, Hematol. Oncol.Clinics North America, 4: 821–833). ATL is an aggressive lymphoid malignancy characterized by rapid progression and by pronounced hypercalcemia. Chemotherapy of ATL is generally ineffective and the disease is often rapidly fatal. ATL develops is a subset of HTLV-1 infected individuals (approximately 1%) with a long clinical latency period prior to onset of lymphoma (20–30 years). As traditional chemotherapeutic approaches to ATL have been largely unsuccessful, a number of newer more innovative therapeutic approaches have been attempted. These include the use of monoclonal antibodies linked to powerful cellular toxins such as the pseudmonas exotoxin (*Saito, T. et al.,* 1994, *Cancer Research* 54: 1059–1064). The monoclonal antibodies used for these studies have been directed against subunits of the interleukin 2 receptor molecule, which is highly expressed on the surface of ATL cells. This molecule is also present to some extent on the surface of certain normal T cells, thus, this approach is only partially selective for ATL cells.

The use of cytopathic viruses for the treatment of malignancy has been proposed (Gutterman and Hersh. lmmunotherapy, in Holland, J. F. and Frei E. eds. Cancer Medicine, Philadelphia, Lea and Febiger, 1982, 1108; Webb, H. E. and Gorden Smith, C. E. Lancet 1970 i 1206–1209; Sutton, Lancet, Lancet 337: 1553, 1991). However, the use of genetically altered viruses to induce specificity has not been described.

U.S. patent application Ser. No. 07/506,947, filed 9 Apr. 1990, (Rabson et. al.) discloses the pILIC HIV plasmid used for the construction of HIV LTR mutants. Rabson et. al. describes the derivation of a circularly permuted version of HIV DNA that could be used for making LTR mutations (Leonard et al. J. Virol. 63: 4919–4924. 1989).

BRIEF DESCRIPTION OF THE FIGURES

FIGS. 1A–1D shows the structure of HIV-1 DNA provirus showing positions of genes and of the long terminal repeats (LTRs).

FIG. 2A is a diagram showing the structure of Recombinant HIV LTRs containing HTLV-1 21 bp Tax-response elements (TREs). The NF-kappa-B and Sp1 binding sites in the wild-type pILIC LTR were deleted and replaced with an Mlu I restriction enzyme cleavage site (M) to create pMlu I. Synthetic oligonucleotides flanked by Mlu I or compatable BssH II (B) sites were then ligated into the Mlu I site of pMlu I to construct the recombinant LTRs shown. MMXB#1 is a control LTR containing two Mlu I restriction sites, one Xba I site (X), and one BssH II site. An oligonucleotide containing the HIV LTR Sp1 site II (open box)was ligated into pMlu I to construct MSpB#26, which now contains a unique Mlu I site adjacent to a single Sp1 site. MSpB#22 was similarly constructed and contains two HIV Sp1 binding sites. Oligonucleotides containing the HTLV-I 21 bp TRE (closed triangle) were then ligate into pMlu I, MSpB#26 and MSpB#22 to create MTaxB#48, MTaxSpB#32, MTaxSpB#6, and MTaxSpB#53.

These LTR mutants were inserted into the pILIC, infectious molecular clone of HIV and transfected into different human cell lines. There was no detectable virus production following A3.01 cell transfected and MT4 cell co-cultivation with the TRE-containing mutants; however, virus stock were recovered following direct transfection of HTLV-1+ MT4 cells with the TRE-containing mutants.

FIGS. 3A and 3B are graphs showing the replication of TRE-containing HIVs in Human T cells. FIG. 3A shows the replication of the various TRE-containing HIVs and the control HIV, pILIC, in HTLV-I Tax expressing cell lines was detected by reverse transcriptase assay and quantitated by phosphorimaging. (FIG. 3A.1, MT4; FIG. 3A.2, MT2; FIG. 3A.3, C8166). All viruses replicated in these cells and replication was associated with cell death as determine by visual inspection, trypan blue dye exclusion, and MTT assay (data not shown, note. FIG. 3B shows the replication of TRE-containing viruses in cells that do contain HTLV-Tax (FIG. 3B.1, PBL; FIG. 3B.2, JE6.1; FIG. 3B.3, A3.01). As compared to the wild-type pILIC plasmid, no evident replication was detected for the TRE-containing viruses.

FIGS. 4A and 4B are graphs illustrating the cytopathicity of TRE-containing HIVs in Human T cell lines. The effects of infection with wild-type or TRE-containing HIVs on cell viability was analzyed in HTLV-I positive MT4 (FIG. 4A), and HTLV-I negative (FIG. 4B.1 and FIG. 4B.2) A3.01 and JE6.1 cells. Viability was determined by the MTT assay (for MT4 cells) or by trypan blue exclusion (A3.01 and JE6.1 cells) and is reported as percent viability of uninfected control cells. Wild-type HIV and TRE-containing HIVs exhibit 100% cell killing in MT4 cells; significant cell killing is only observed with wild-type virus infection in A3.01 and JE6.1 cells.

SUMMARY OF THE INVENTION

In one embodiment, the present invention pertains to a genetically altered human immunodeficiency virus type 1 (HIV-1) which replicates only in human CD4+ cells that express the Tax protein of Human T-cell Lymphotropic Virus Type I (HTLV-I), wherein the HIV long terminal repeat (LTR) promoter and enhancer sequences (NF-kappa-B and Sp1 binding sites) of the genetically altered human immunodeficiency virus type 1 have been replaced by two copies of the HTLV-I LTR 21 base pair repeat Tax-responsive element (TRE).

In another embodiment, the present invention pertains to a method for killing HTLV-1 infected cells in humans with HTLV-1 disease (HTLV-1 tumors and HTLV-associated myelopathy/tropical spastic paraparesis) which comprises administering to the human a therapeutically effective amount of a genetically altered human immunodeficiency virus type 1 (HIV-1) which replicates only in human CD4+ cells that express the Tax protein of Human T-cell Lymphotropic Virus Type I (HTLV-I), wherein the HIV long terminal repeat (LTR) promoter and enhancer sequences (NF-kappa-B and Sp1 binding sites) of the genetically altered human immunodeficiency virus type 1 have been replaced by two copies of the HTLV-I LTR 21 base pair repeat Tax-responsive element (TRE).

In yet another embodiment, the present invention pertains to a human immunodeficiency virus replication defective vector containing long terminal repeat mutants for a genetically altered human immunodeficiency virus type 1 (HIV-1) which replicates only in human CD4+ cells that express the Tax protein of Human T-cell Lymphotropic Virus Type I (HTLV-I), wherein the HIV long terminal repeat (LTR) promoter and enhancer sequences (NF-kappa-B and Sp1 binding sites) of the genetically altered human immunodeficiency virus type 1 have been replaced by two copies of the HTLV-I LTR 21 base pair repeat Tax-responsive element (TRE), wherein the vector expresses genes encoding cytotoxic proteins.

DETAILED DESCRIPTION OF THE INVENTION

This invention relates to genetically engineered human cytopathic viruses which are altered by recombinant DNA techniques to specifically replicate in human tumor cells. Specifically, the human immunodeficiency virus type 1 (HIV-1) was genetically altered such that it will only replicate in human CD4+ cells that express the Tax protein of the Human T-cell Lymphotropic Virus Type I (HTLV-I). This alteration was accomplished by replacement of the HIV long terminal repeat (LTR) promoter and enhancer sequences (NF-kappa-B and Sp1 binding sites) by two copies of the HTLV-I LTR 21 base pair repeat Tax-responsive element (TRE). As set out in FIG. 2, the NF-kappa-B and Sp1 sites that form the obligate enhancer of transcription of HIV, were deleted from the pILIC permuted wild-type HIV molecular clone, and replaced with an Mlu I restriction enzyme site (pMlu1). Oligonucleotides containing the TRE sequence were then inserted at this site. In particular, recombinant virus MTaxB #48 contains two copies of the TRE element in the reverse orientation from their orientation in the HTLV-I promoter. Recombinant virus MTaxSpb#53 retains two Sp1 site (duplication of Sp1 site II in the HIV LTR) and contains three copies of the TRE element in the "sense" orientation. Introduction of the TREs into the HIV-1 LTR results in production of an HIV that replicates in, and is cytotoxic for HTLV-1-infected cells (expressing the HTLV-I Tax protein) but does not efficiently replicate in CD4+ cells lacking HTLV-I Tax, such as normal human peripheral blood mononuclear cells (see FIG. 3).

Genetically modified HIV, either as replication competent virus or as replication defective HIV vectors carrying genes encoding toxic products, may be useful as selectively cytotoxic therapeutic agents for therapy of HTLV-1-induced malignancies. In order to generate an HIV DNA clone specifically tropic for HTLV-1 infected cells, we have taken advantage of the HTLV-specific transactivation pathway in which the HTLV-1 Tax protein interacts with cellular transcriptional factors to transactivate expression directed by the HTLV-1 LTR through the Tax-response elements (TREs) as shown in FIGS. 1C and 1D. Furthermore, this approach, in which expression of cytopathic retroviral sequences is directed HTLV-1 Tax protein in HTLV-1 infected cells activating a promoter containing the 21 base pair TREs, could be readily adapted to currently utilized, state of the art murine leukemia virus (MLV)-based gene therapy vectors to develop gene therapy vectors that could selectively kill HTLV-1 infected cells.

The DNA sequence called the Tax response element or TRE is the target for the action of the HTLV-1 transactivator of transcription, the Tax protein. By substituting copies of the HTLV-1 LTR TRE sequences for the HIV-1 LTR Sp1 and NF-kappa-B binding sites, we have constructed a molecular clone of HIV, that produces virus that will selectively replicate in and kill, cells producing the HTLV-1 Tax protein.

Previous studies have suggested that the HIV LTR enhancer/promoter sequences contribute to the replication ability of HIV in different T cell lines; mutation of these sequences can alter HIV tropism. In this study, we have utilized site-specific mutagenesis to generate variants of HIV that exhibit tropism for HTLV-I Tax expressing CD4+ T cells. The wild-type HIV LTR NF-kappa-B and Sp1 sites in an infectious molecular clone of HIV-1, were replaced with sequences derived from the 21 bp Tax-response element (TRE) from the HTLV-I LTR, either in the presence or absence of Sp1 binding sites. Infectious recombinant virus was generated following transfection of HTLV-I+, MT4 cells, and was assayed for infectivity for a variety of human CD4+ T cells. The TRE-containing HIVs (either with or without the Sp1 binding sites) replicated in, and were cytopathic for a number of Tax-expressing T cell lines, including MT4, MT2, and C8166 cells. In contrast, the TRE-HIVs did not replicate efficiently in CD4+ T cells lacking Tax expression, including (HEM, Jurkat, Molt 4, and human peripheral blood mononuclear cells. Transient transfections suggested that Tax-TRE interactions could account for the observed replication specificity. Transfection of Jurkat cells with a plasmid containing the TRE-HIV-LTR directing expression of the CAT gene resulted in low level CAT activity which was only weakly activated by either HTLV-1 Tax or HIV Tat co-transfection. Co-transfection of both Tat and Tax resulted in marked synergistic transactivation of TRE-HIV LTR expression, suggesting that Tax-TRE transcriptional activation could productively interact with HIV Tat. These studies illustrate that it is possible to use Tax-TRE interactions to generate a virus cytopathic for Tax-expressing cells and raise the possibility that the Tax-TRE transactivation system could be used in the design of gene therapy vectors specifically cytotoxic for HTLV-I+ cells.

The novel feature of this invention is that a cytopathic human virus (in this case HIV), is targeted to destroy human tumor cells by altering the promoter elements of the cytopathic virus such that it will only replicate in specific tumor cells. This feature provides a unique mechanism for selectively destroying tumor cells. Gene expression of a cytopathic virus will only occur in tumor cells expressing either transcriptional activators of an oncogenic virus (such as HTLV-I) or altered transcription factors unique to the malignant cell (for example, altered versions of the p53 tumor suppressor gene). In the example provided here, HIV is altered such that it will selectively replicate in HTLV-I expressing cells, such as HTLV-I+lymphoma cells (Adult T-cell lymphoma or ATL) or HTLV-I infected cells in the chronic neurological disorder, Tropical Spastic Paraparesis/HTLV-associated myelopathy (TSP/HAM).

HTLV-I associated lymphoma (ATL) is a devastating, usually fatal lymphoid malignancy. The genetically-engineered HIV will specifically replicate in, and kill HTLV-I infected CD4+ T lymphocytes including HTLV-I lymphoma cells. This cytopathic virus could provide potentially curative therapy to individuals with ATL whose malignancy has failed to respond to other therapeutic approaches. This recombinant virus could also affect the development and progression of TSP/HAM. The approach described herein is not limited to HIV-based vectors and HTLV infection. For example, many human carcinomas contain genetic alterations in the p53 tumor suppressor gene that alter its specificity as a transcriptional activator. Other (i.e., non-HIV) cytopathic human viruses, such as adenoviruses, could be engineered such that critical viral gene expression (for example early gene promoters of adenovirus) becomes dependent on expression of mutant forms of p53, but is not activated by wild-type p53.

The major disadvantage of this invention is the dependence on replication-competent cytopathic viruses (Such as HIV) for tumor cell destruction. This raises the potential problem that the replication competent virus might develop secondary mutations that would allow it to replicate in normal human cells, potentially resulting in serious adverse effects, possibly including development of acquired immunodeficiency syndrome (AIDS). This disadvantage could be overcome by the use of replication defective viruses which would express cytotoxic genes under the control of the tumor cell specific promoter. For example, instead of using replication competent HIV, one could engineer HIV to express the herpes thymidine kinase (HSV tk) gene under the control of the TREs. The replication-defective HIV could still provide a vector for entry of the defective virus into CD4+ T cells. Following treatment with ganciclovir, only cells expressing HSV tk (i.e., Tax-expressing tumor cells) would be killed. A second potential disadvantage for treatment of ATL by this method is that ATL tumor cells in vivo constitutively express only very low to undetectable levels of Tax. If this is true, a recombinant virus whose expression is dependent on Tax would not replicate. However, culture of ATL cells ex vivo results in rapid induction of expression of Tax. This raises the possibility that Tax expression could be induced in vivo, potentially by cytokine treatment. If this were true, patients could be briefly treated by the appropriate cytokine (possibly interleukin-2) prior to treatment with the cytotoxic virus. Another potential disadvantage could be the development of effective immune response to the cytopathic virus. This may be less problematic for our example of HIV infection in HTLV-I lymphoma; the immune response to HIV may be somewhat less effective than to other viruses. Furthermore, HTLV-1 disease may be associated with variable degrees of immunosuppression. Nonetheless, this remains a potential problem.

The experiments presented here outline the generation of genetically altered, replication-competent, HIV which exhibits specific cytotoxicity for HTLV-1 infected cells. There are clearly multiple safety considerations that would have to be addressed prior to the use of such a replication-competent, altered HIV in patients with HTLV-1-induced lymphomas. Two safer alternatives may be easily envisaged which would involve the generation of replication-defective retroviral vectors which utilize the specificity engendered by the recombinant HIV LTR containing the Tax-response elements.

In one case, the TRE-containing HIV LTRs could be engineered into replication-defective HIV particles generated through an HIV-1 packaging system. Several such HIV-1 packaging systems have been reported (Shimada, T., et al., 1991, *J. Clin. Invest.* 88: 1043–1047, Poznansky M., et al., 1991, *J. Virol.* 65: 532–536, Page, K. A. et al., 1990, *J. Virol.* 64: 5270–5276). HIV-based vectors could be easily constructed containing the recombinant TRE-containing HIV LTR directing the expression of a defective HIV genome containing any one of a variety of toxic gene products ("suicide" genes) such as the herpes simplex virus thymidine kinase gene that encodes an enzyme that is cytotoxic if cells are treated with gancyclovir). These genes could be easily inserted into a number of regions in the HIV genome as described for marker genes used to monitor HIV drug resistance (Strair, R. L. et al., 1993, *Nucleic Acid Res.* 21: 4836–4842), including the HIVnef open reading frame The HIV tat gene could be included to increase expression directed from the TRE-containing LTR. DNA from these replication defective HIV genomes would be transfected into HIV packaging cell lines to generate defective HIV particles containing the recombinant vector genome with the suicide gene flanked by the TRE-containing LTRs. Such a recombinant HIV particle would be capable of infecting CD4+ T cells, including HTLV-1 tumor cells. Based on the experiments outlined in this application, it can easily be expected that such a replication-defective HIV would only express the protein encoded by the "suicide" gene in cells that express the HTLV-1 Tax protein. Thus, selective toxicity for HTLV-1 tumor cells would be provided by the Tax protein selectively directing gene expression in these cells.

A second alternative to using replication-competent HIV for the selective destruction of HTLV-1 tumor cells is the generation of recombinant murine leukemia-based vectors that would express toxic gene products selectively in HTLV-1 Tax expressing cells based on the use of the TRE elements to direct synthesis of the "suicide gene".

EXAMPLES

The use of in vivo therapy of malignancies with cytotoxic retroviral-based vectors raises a number of important problems related to the efficiency of vector delivery to tumor cell targets and the safety of the retroviral vector systems used. The HIV-1 based vectors for selective biological destruction of tumor cell described in the present application will face similar problems. However, based on their success in killing HTLV-1 infected cells in tissue culture, it is likely that these vectors will find a more practical application in the destruction of tumor cells ex vivo. The rationale, therapeutic approach, and advantages offered for the use of this invention as an ex vivo reagent for purging tumor cells from hematopoietic stem cell populations in the treatment of Adult T-cell Leukemia are outlined below.

HTLV-1 induced Adult T-cell Leukemia/Lymphoma (ATL) is a devastating disease. Acute ATL is a rapidly progressive and generally fulminant disease with a median survival of untreated disease of 3 to 4 months from the time of diagnosis (Leukemia Study Group, (1991) Leuk. Res. 15, 81–90; Shimoyama, M. (1991) Br. J. Haematol. 79, 428–37). Treatment of ATL with combination chemotherapy may effectively achieve an initial cytoreduction, but relapse is almost universal and responses to additional chemotherapeutic regimens generally provide short-term benefit at best (Shimoyama, M. (1991) Br. J. Haematol. 79, 428–37; Bunn, P. J., Schechter, G. P., Jaffe, E., Blayney, D., Young, R. C. Matthews, M. J., Blattner, W., Broder, S., Robert, G. M., & Gallo, R. C. (1983) N. Engl. J. Med. 309, 257–64; Broder, S., Bunn, P. J., Jaffe, E. S., Blattner, W., Gallo, R. C., Wong, S. F., Waldmann, T. A. & DeVita, V. J. (1984) Ann. Intern. Med. 100, 543–57).

One successful approach to the management of patients with other types of lymphoproliferative diseases that are refractory to treatment has involved the use of high dose chemotherapy (or chemo-radiotherapy) followed by hematopoietic stem cell transplantation (Armitage, J. 0, & Antman, K. H. (1992) High dose cancer therapy (Williams and Wilkins, Baltimore); Kessinger, A. (1992) In Reestablishing hematopoiesis after dose intensive therapy with peripheral stem cells, eds., Armitage, J. & Antman, K. H. (Williams and Wilkins, Baltimore), pp. 182–194; Reed, C, E. & Kessinger, A. (1994) Autologus Bone Marrow Transplantation (Churchill Livingstone, N.Y.). Treatment for these patients is undertaken with doses of chemotherapy that are myeloablative. Hematopoietic stem cell transplantation is then utilized to rescue the patient's hematopoietic capacity. For example, high dose chemo-radiotherapy followed by allogeneic bone marrow transplantation has been utilized in the successful management of a variety of patients with poor prognosis hematologic malignancies. Even patients with acute lymphocytic leukemia (ALL) who have had an extremely poor prognosis (i.e., adults whose leukemic cells contain a translocation which fuses the bcr and abl genes) have occasionally been cured with allogeneic bone marrow transplantation (Barret A. J., Horowitz, M. M., & Ash R. C., (1992) Blood 79 3067). Similarly, patients with intermediate grade non-Hodgkin's lymphomas and high grade non-Hodgkin's lymphomas that have relapsed after initial chemotherapy and are otherwise incurable, have been treated with high dose chemotherapy followed by hematopoietic stem cell transplantation (Kessinger, A. (1992) In Reestablishing hematopoiesis after dose intensive therapy with peripheral stem cells, eds., Armitage, J. & Antman, K. H. (Williams and Wilkins, Baltimore), pp. 182–194; Reed, C, E. & Kessinger, A. (1994) Autologus Bone Marrow Transplantation (Churchill Livingstone, N.Y). In contrast to allogeneic transplantation, the majority of these patients have been treated with high dose chemotherapy followed by autologous hematopoietic stem cell transplants. This approach has been demonstrated to be successful for approximately 25%–50% of highly selected groups of patients. The efficacy of high dose chemotherapy (or chemo-radiotherapy) followed by hematopoietic stem cell transplantation is dependent upon adequate tumor cell kill by the high dose therapy, and rescue of the patient's hematopoietic capacity by the infused stem cells. In an allogeneic transplant, the infused cells are obtained from an HLA-matched donor, and the cells may also ultimately develop an immune response against the leukemia providing an advantage for allogeneic as opposed to autologous transplantation in some diseases. In addition, the donor stem cells in an allogeneic transplant will not have contaminating malignant cells. Nevertheless, allogeneic transplantation is a very high risk procedure complicated by the need for an HLA-matched donor, the presence of prolonged immunosuppression, leukopenia and thrombocytopenia, and marked toxicity when graft versus host disease occurs. Autologous hematopoietic stem cells are not associated with significant persistent graft versus host diseases, making autologous stem cell transplantation a less toxic procedure to withstand. However, there is no graft versus leukemia effect and the stem cells must be harvested before the high dose chemotherapy is administered, resulting in the possible presence of contaminating malignant cells in the stem cell preparation.

Patients with ATL will often respond to standard dose combination chemotherapy regimens such as m-BACOD (methotrexate, bleomycin, cyclophosphamide, doxorubicin, and dexamethasone) or ProMACE-CytaBOM (cyclophosphamide, doxorubicin, etoposide, cytarabine, bleomycin, vincristine, methotrexate, and prednisone) with a complete or partial remission (Leukemia Study Group, (1991) Leuk. Res. 15, 81–90; Shimoyama, M. (1991) Br. J. Haematol. 79, 428–37; Bunn, P. J., Schechter, G. P., Jaffe, E., Blayney, D., Young, R. C. Matthews, M. J., Blattner, W., Broder, S., Robert, G. M., & Gallo, R. C. (1983) N. Engl. J. Med. 309, 257–64; Bunn, P. J. (1989) West. J. Med. 150, 578–9). Therefore, it is possible to achieve initial malignant cell killing in these patients. However, cure is not achieved, because even at the time of complete remission, it is estimated that $10^8$ leukemic cells may persist, and some of those cells are refractory to standard dose chemotherapy. The susceptibility of these residual malignant cells to high dose chemotherapy is unknown. By analogy to the treatment of other lymphoproliferative diseases, it is possible much greater leukemia cell killing, resulting in sustained remissions and even cure, could be obtained with very high dose chemotherapy if the patient's hematopoietic capacity could be rescued by a non-contaminated source of hematopoietic stem cells. As set out above, this approach has been successfully applied in the management of patients with other types of lymphoproliferative diseases. The paucity of prior reports of treatment of patients with ATL with very high dose chemotherapy followed by hematopoietic stem cell transplantation precludes an assessment of response rates and durability of response after such therapy. There is, however, a single reported case of a significant and prolonged remission in a patient with ATL who was treated with very high dose chemotherapy (carmustine, etoposide, cytarabine, and melphalan) supported by hematopoietic growth factors (Brito-Babapulle, F., Arya, R., Griffiths T., Pagliuca, A. & Mufil G. J. (1992) Lancet 339, 133–134). In addition, two allogeneic bone marrow transplants involving HTLV-1 infected patients have been performed at Yale New-Haven Hospital. One of these patients had ATL and died of infectious causes in a complete remission two months after high dose chemo-radiotherapy and an allogeneic transplant (Strair, R. K. & Rappoport, J. M. (1995), unpublished observations). A second HTLV-1 infected patient underwent an allogeneic transplant for aplastic anemia and is reported to be doing well two years after transplantation. This latter patient demonstrates the ability of hematopoiesis to be re-established in an HTLV-1 infected patient and suggests that transplantation of an HTLV-1 infected patient may be associated with prolonged survival.

The objective of high dose chemotherapy followed by transplantation with hematopoietic stern cells is to achieve an adequate cytoreduction of malignant cells to provide long term benefit to the patient (Reed, C, E. & Kessinger, A. (1994) Autologus Bone Marrow Transplantation (Churchill Livingstone, N.Y.)). One potential objection to the use of such an approach to treat patients with an HTLV-1 associated malignancy is that it would likely be impossible to eradicate HTLV-1. However, the objective of therapy is to eliminate the clone of malignant cells. Persistence of the virus might not alter the benefit of a successful procedure, because only a very small percentage of HTLV-1 infected patients develop ATL, generally after a long latent period. Furthermore, hematopoietic stem cells are not infected with HTLV-1 (Nagafuji, K., Harada, M., Teshima, T., Eto, T., Takamatsu, Y., Okamura, T., Murakawa, M., Akashl, K. & Niho, Y. (1993) Blood 82, 2823—8) and hematopoietic recovery in the presence of HTLV-1 has been demonstrated (Strair, R. K. & Rappoport, J. M. (1995), unpublished observations). Thus, persistence of HTLV-1 would be unlikely to result in future malignant complications.

Another consideration in the use of high dose chemotherapy and stem cell transplantation in the treatment of ATL is potential intolerance of the treatment-associated immunosuppression, superimposed on the immunosuppression that is often associated with the underlying disease. Nevertheless, the tolerability of standard dose combination chemotherapy administered over 6 months has been established.

A third potential objection to attempts to treat ATL patients with high dose chemotherapy followed by autologous stem cell transplantation is the likelihood of contamination of the harvested autologous hematopoietic stem cell with malignant cells. This contamination is likely, since there is a high prevalence of malignant cells in both bone marrow and blood, the two potential sources of hematopoietic stem cells. Therefore, the use of autologous stem cell transplantation will require the means to purge hematopoietic stem cells of contaminating malignant cells. The potential importance of "purging", in association with high dose therapy and stem cell transplantation in some lymphoproliferative diseases with frequent blood and bone marrow involvement, has been suggested by clinical studies of patients with low grade B-cell lymphomas and a group of patients who frequently have malignant cells in both blood and bone marrow (Gribben, J. G., Freedman, A. S. & Neuberg D. (1991) N. Engl J. Med. 325, 1525). The approach proposed in the present invention is the application of applicants' mutant HIVs containing the HTLV-1 Tax Response Elements (TREs), which exhibit specific cytotoxicity for HTLV infected cells, in the purging of ATL cells from preparations of hematopoietic stem cells, prior to autologous stem cell transplantation.

The clinical approach is ex vivo "purging" of autologous hematopoietic stem cells. Acute ATL patients are treated with standard dose chemotherapy and those patients achieving a complete remission would have samples of blood and bone marrow assessed by molecular techniques for the prevalence of malignant cells. Samples that have the lowest prevalence contaminating malignant cells serve as the source of hematopoietic stem cells. Partial purification of mobilized hematopoietic stem cells by antibody affinity is used to generate a population of autologous hematopoietic stem cells to be treated with the recombinant TRE-HIV vectors for purging of HTLV-1 infected cells. It is known that hematopoietic stem cells express CD34. Affinity techniques that utilize a monoclonal antibody to CD34 are available in a column or magnetic bead separation (14). These affinity techniques allow the isolation of cells that are 50–70% pure with respect to CD34 and only $2–4\times10^6$ CD34+ cells/kg are required to achieve hematopoietic reconstitution (Kessinger, A. (1992) In Reestablishing hematopoiesis after dose intensive therapy with peripheral stem cells, ed., Armitage, J. & Antman, K. H. (Williams and Wilkins, Baltimore), pp. 182–194). In addition, ATL cells do not express CD34 and early hematopoietic stem cells obtained from HTLV-1 infected volunteers or ATL patients do not contain HTLV-1 viral sequences (Fujita, M., Murata, K. & Shiku, H. (1994) Blood 84, 2591–2596). Therefore, CD34 affinity purification provides a great degree of stem cell enrichment and can be followed by viral infection with a TRE-modified HIV encoding HSV tk (i.e., a replication-defective HIV vector expressing a suicide gene). The infection of this population of cells containing hematopoietic stem cells with a recombinant retrovirus which has been modified to specifically express a suicide gene in HTLV-1 infected cells purges the stem cells of contaminating ATL cells. Treated stem cells are then be administered to the patient after high dose chemotherapy.

This ex vivo treatment approach allows specific infection and killing of ATL cells contaminating hematopoietic stem cell preparations from ATL patients. This treatment approach renders these preparations suitable for re-infusion and hematopoietic stem cell rescue of patients subjected to high-level, bone marrow ablative chemotherapy that may be curative for ATL.

The following example illustrates the preparation of a circularly single LTR infectious molecular clone of HIV DNA.

Figures 1, 1A:
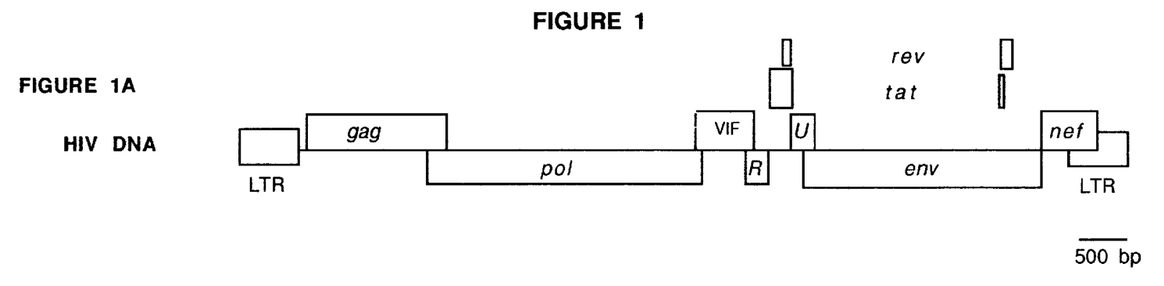
Figure 1B:
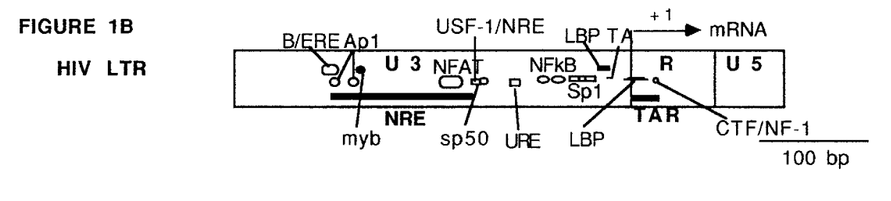
FIG. 1B shows the structure of HIV-1 LTR showing positions of cis-acting regulatory elements including NF-kappa-B and Sp1 binding sites.
Figure 1C:
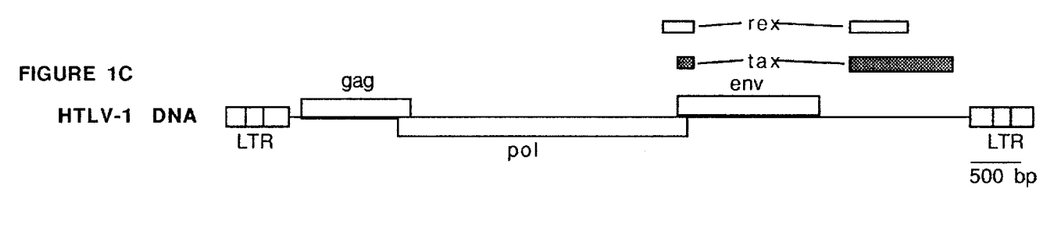
FIG. 1C shows the structure of the HTLV-1 DNA provirus showing positions of genes including the tax gene.
Figure 1D:
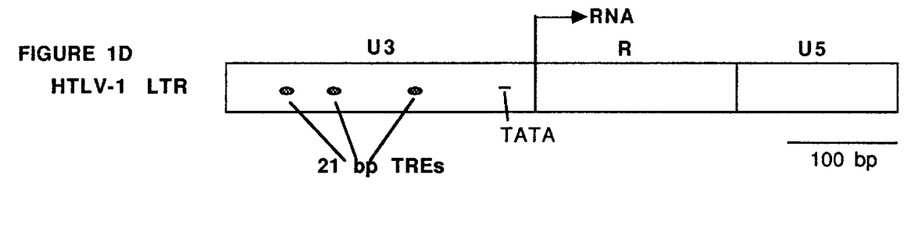
FIG. 1D shows the structure of the HTLV-1 LTR showing positions of the 21 base pair Tax-responsive elements (TREs).

A complete LTR element linked to genes situated near both the 5' and 3' ends of the viral genome was generated by ligating the 912-bp HindIII-SDhI fragment (V5 sequences) to the 1,141 bp BamHI-HindIII fragment (U3+R sequences) (FIG. 1.). This reconstructed LTR (FIG. 1B) was then molecularly clones into BamHI-SDhI-cleaved M13 mp19 DNA to facilitate the introduction of specific mutations by oligonucleotidedirected, site-specific mutagenesis (Zoller et al., 1983. D~IA 3: 479–488) as modified by Kunkel (1985, Proc. Natl. Acad. Sci ~'SA 82: 488–492). After confirmation of the mutagenized segments by DNA sequence analysis (Sanger et al. 1977, Proc. Natl. Acad. Sci. USA 74: 5463–5g67), the LTR elements were excised from the M13 vector by cleavage with BamHI and SphI. The wild-type (pILIC) LTR and one Sp1 mutant (pSpB) LTR segment were ligated to the 7.4-kilobase (kb) SphI-XhoI internal HIV fragment from pNL4—3 (FIG. 1C) and then inserted into plasmid vector pIBI20, which had been cleaved with BamHI and XhoI. All other mutagenized LTR segments were ligated to the 7.0-kb SPhI-BamHI fragment from pNL4—3 (FIG. 1D) and cloned into pUC19 at the BamHI site. Another set was cloned into p~C8 following the same procedure. pUC8 is particularly advantageous because this vector contains fewer restriction enzyme sites in the poly-linker flanking the ILIC sequences. The structures of the resultant single LTR provirus plasmid DNAs were confirmed by cleavage with BamHI, XhoI, or HindIll and by double digestion with BamHI plus SPhI. The mutagenized segments of each LTR were also resequenced in the reconstructed single LTR proviral clones before use in biological assays.

Figure 2A:
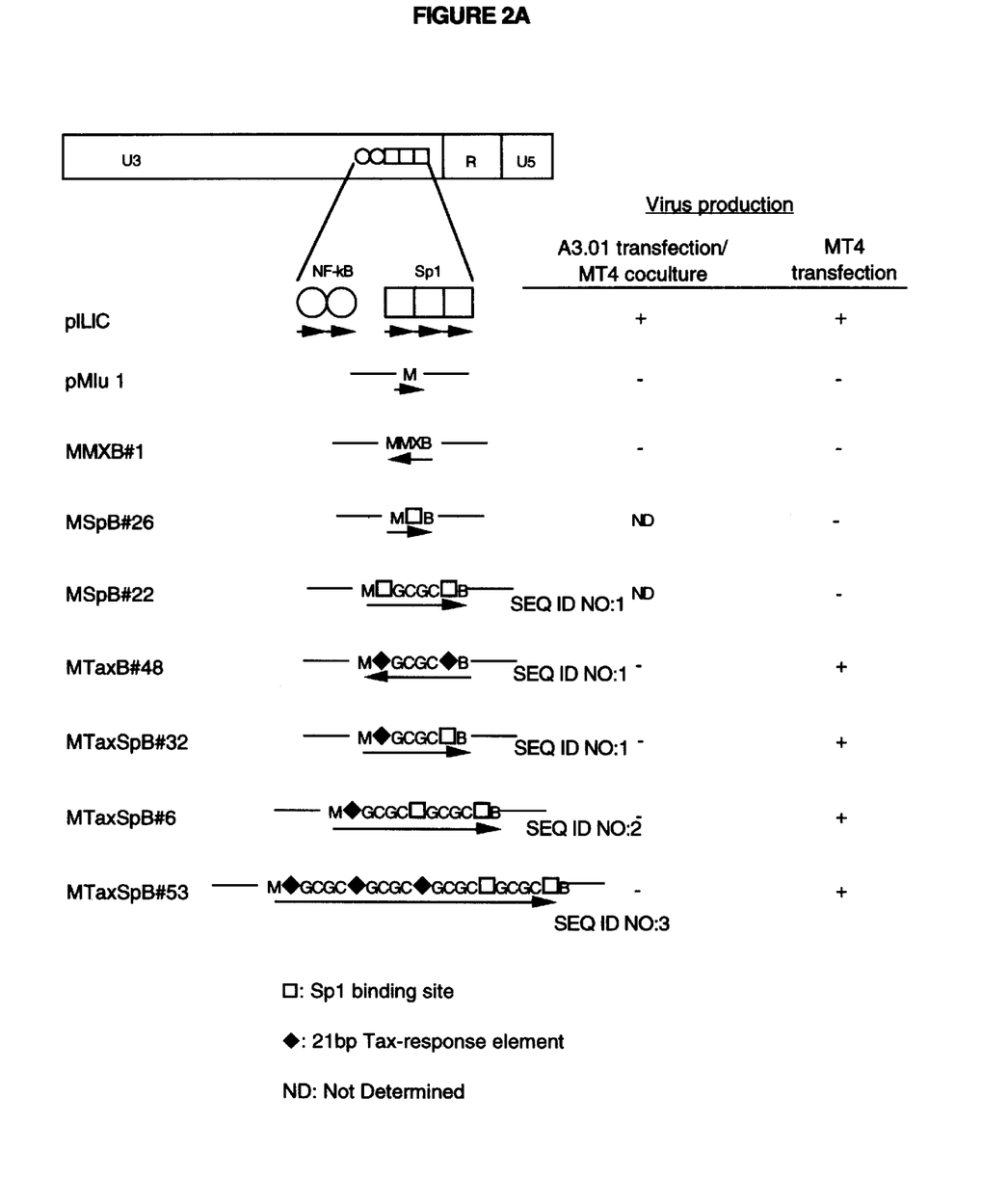
Figure 2B:
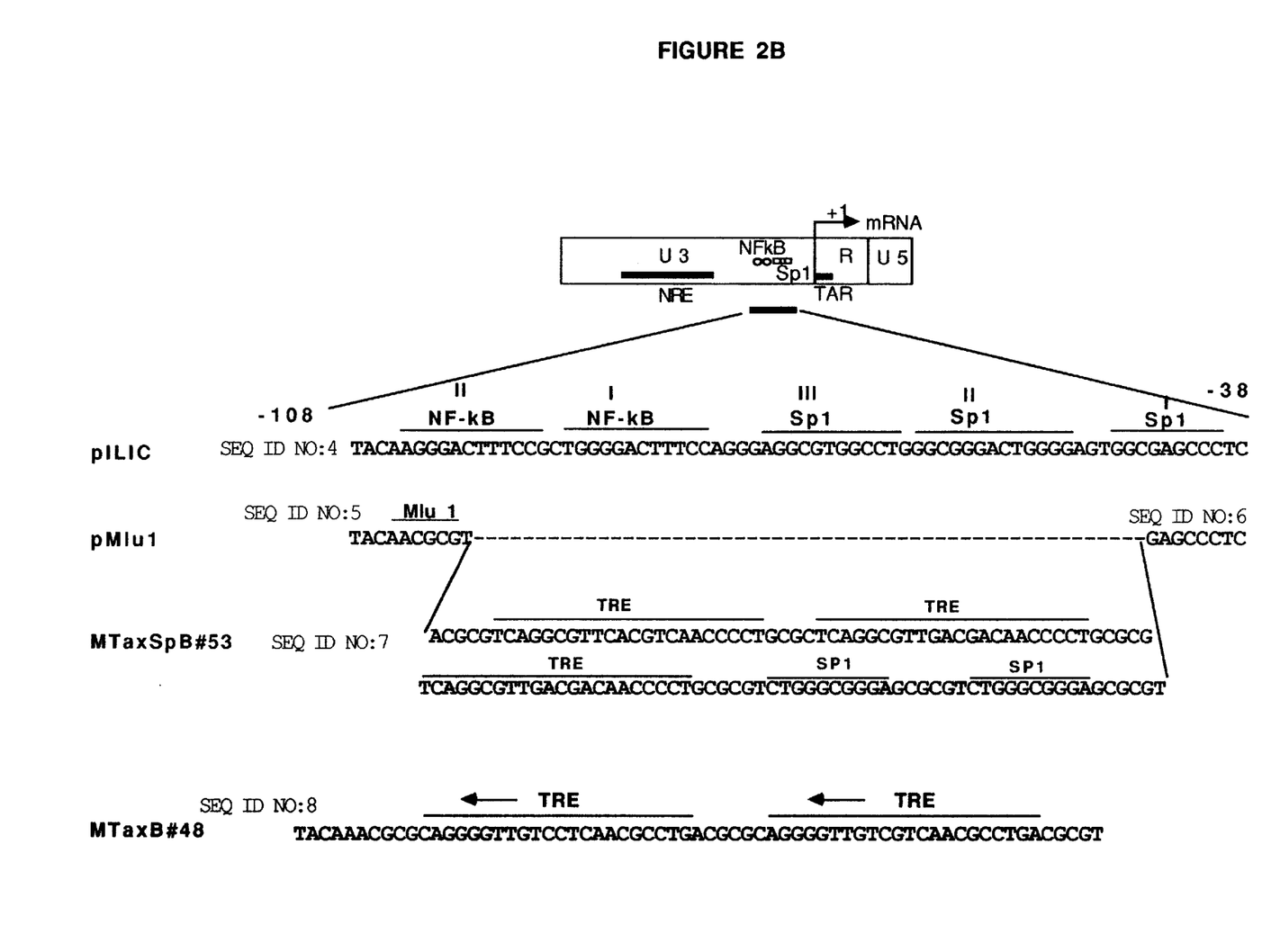
FIG. 2B. Nucleic acid sequence of the Wild-type pILIC LTR in the region of the NF-kappa-B and Sp1 binding sites, and of the pMLul, pMTAXSpB#53 and pMTAx#48 mutant LTRs.

The DNA from the ILIC molecular clone of HIV was utilized to construct HIV clones containing the HTLV-1 TRE sequences. The structure of the wild-type and mutated LTRs is shown in FIG. 2. The initial mutagenic step was performed on the Bam H1 to Sph I segment from pILIC, containing the complete HIV LTR sequence, inserted into the pALTER mutagenesis vector (Promega). Site-specific mutagenesis was performed using the Altered Sites in vitro Mutagenesis System (Promega, Madison, Wis.) according to manufacturer's instructions. In this initial step, the HIV LTR Sp1 and NF-kappa-B binding sites were deleted and replaced with a single MluI restriction enzyme cleavage site. The MluI-containing LTR was replaced into the pILIC HIV infectious molecular clone, in place of the wild-type LTR sequences to generate the pMluI clone. The inserted LTR Mlu I site was unique to the p MluI provirus, and was used for the insertion of oligonucleotides containing transcription factor binding sites. The MMXB#1 clone was created by insertion of an oligonucleotide containing MluI, Xba I, and BssHII restriction enzyme sites, and served as a negative control for subsequent experiments. One or two copies of an HIV I Sp1 binding site were inserted into the p Mlu I DNA Mlu I site by ligation of Sp1 oligonucleotides flanked by Mlu I and BssHII compatible DNA overhangs. Proviruses containing one or two Sp1 sites, with a regenerated unique Mlu I site, were obtained and designated MSpB#26 and mSpB#22 respectively. pMlu 1, pMSpB#26 and pmSpB#22 were used as substrates for the insertion of oligonucleotides containing the HTLV-1 TREs into the HIV LTR. Four TRE-containing LTRs were obtained: pMTaxB#48 contains two TREs present in the reverse orientation with respect to the HIV LTR direction of transcription; pMTaxB#32 contains a single TRE and single Sp1 site in the same orientation as HIV transcription; pMTaxSpB#6 contains one TRE and two Sp1 sites in the same orientation as HIV transcription; and pMTaxSpB #53 contains three TREs and two Sp1 sites in the same orientation as HIV transcription. The DNA sequences of the wild-type HIV LTR, pMluI, and two TRE-containing LTRs (pMTaxB#48 and pMTaxB#53, both studied in greater detail below) are shown in FIG. 2B The biological activity of the wild-type and mutated LTRs was assayed following transfection of human CD4+ T cells, which are capable of supporting HIV replication. As expected, DEAE-mediated DNA transfection of the wild-type HIV (pILIC) into A3.01 CD4+ T cells, followed by co-cultivation with MT4 cells (a CD4 +, HTLV-1+ T cell line) resulted in replication of HIV (FIG. 2A). No virus was recovered following a similar transfection and cocultivation protocol for pMlu1, pMSpB#26, pMSpB#22, or any of the TRE-containing viruses. In order to try to directly rescue replication of the TRE-containing viruses in HTLV-1 Tax-expressing cells, transfections were repeated directly into MT4 cells, thus obviating the need for a co-cultivation step. In contrast to the previous results, transfection of all of the TRE-containing viruses resulted in recovery of infections HIV (FIG. 2A). Viral stocks of the wild-type and TRE-containing HIVs were prepared in MT4 cells and were used to assess the replication properties of the TRE-containing viruses in different human CD4+ T cells.

Figure 3A:
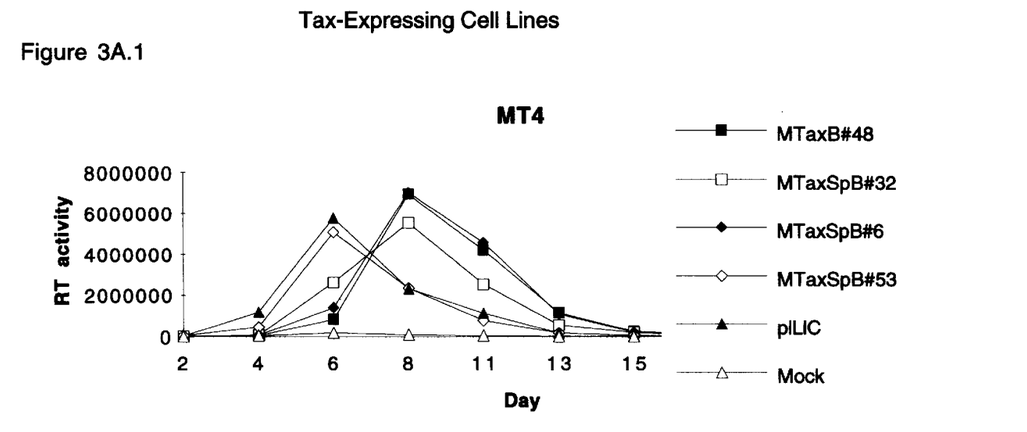
Figure 3A:
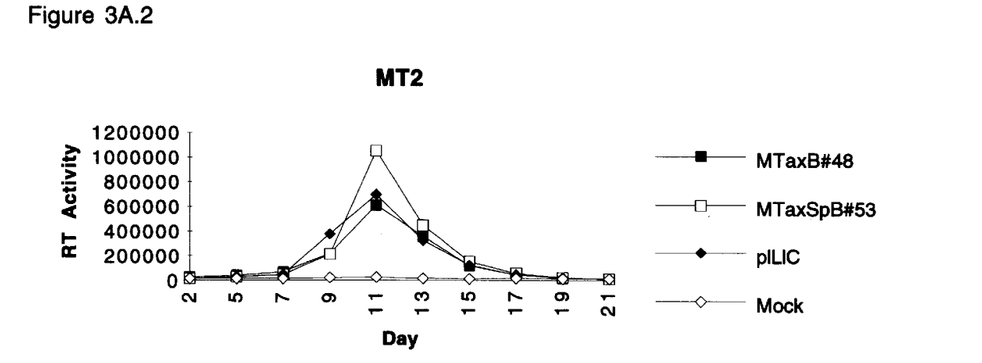
Figure 3A:
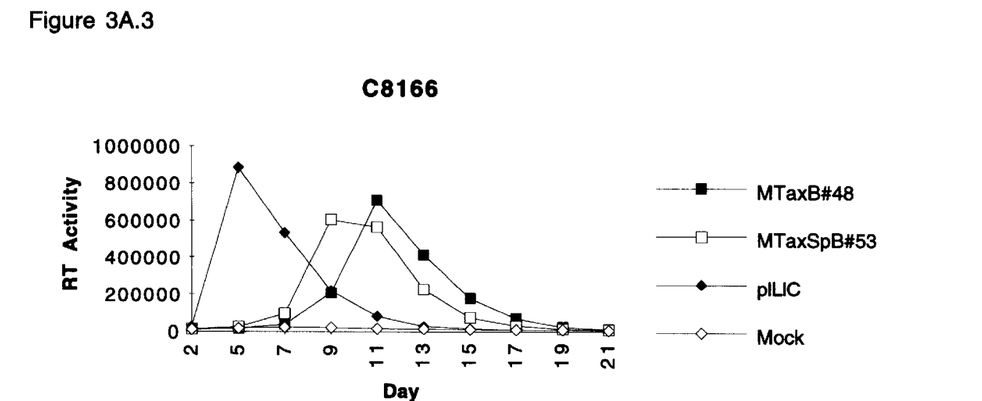
Figure 3B:
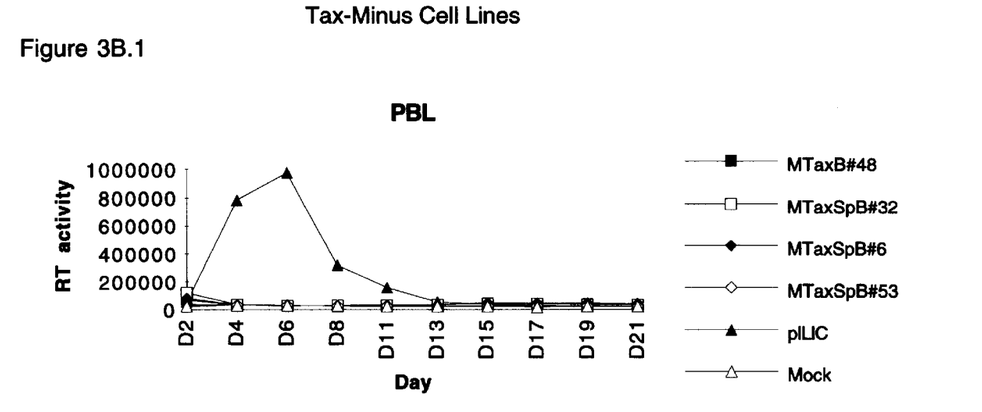
Figure 3B:
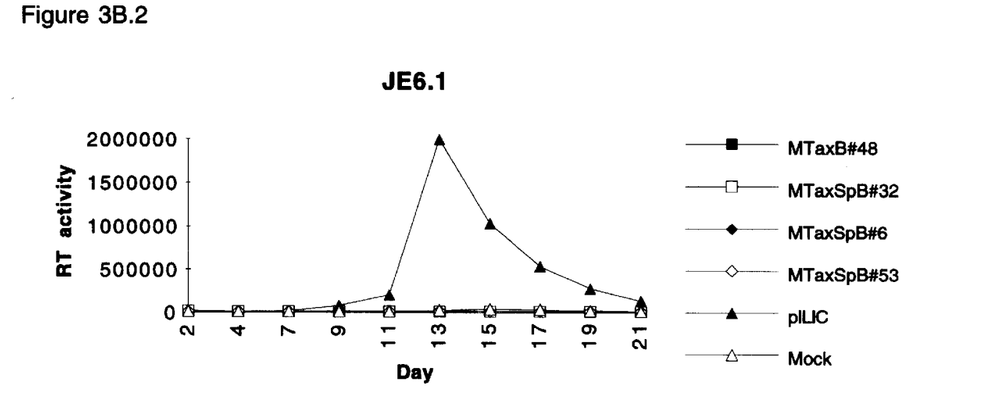
Figure 3B:
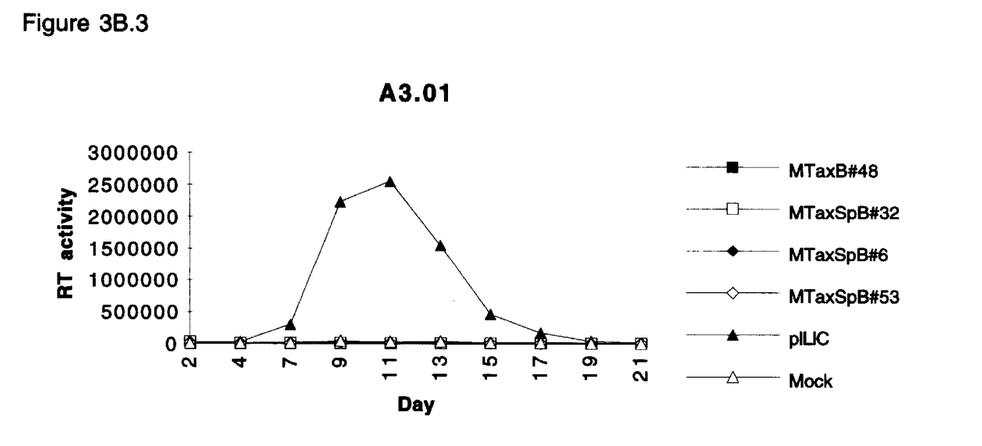

As shown in FIG. 3A, the wild-type and TRE-containing HIVs replicated efficiently in three different HTLV-1 positive cell lines; MT4, MT2m, and C8166 cells. In contrast, as shown in FIG. 3B, no replication of the TRE-containing viruses was observed in cell lines negative for HTLV-1, including the JE6. 1subclone of Jurkat cells, the A3.0 1 clone of CEM cells, the H9 clone of Hut 78 cells (not shown), and human peripheral blood mononuclear cells. Wild-type HIV replicated efficiently in all of these HTLV-1 negative cells. These results suggest that insertion of the HTLV-1 TRFs into the HIV LTR results in generation of an infectious HIV that selectively replicates in HTLV-1 Tax expressing cells.

Figure 4A:
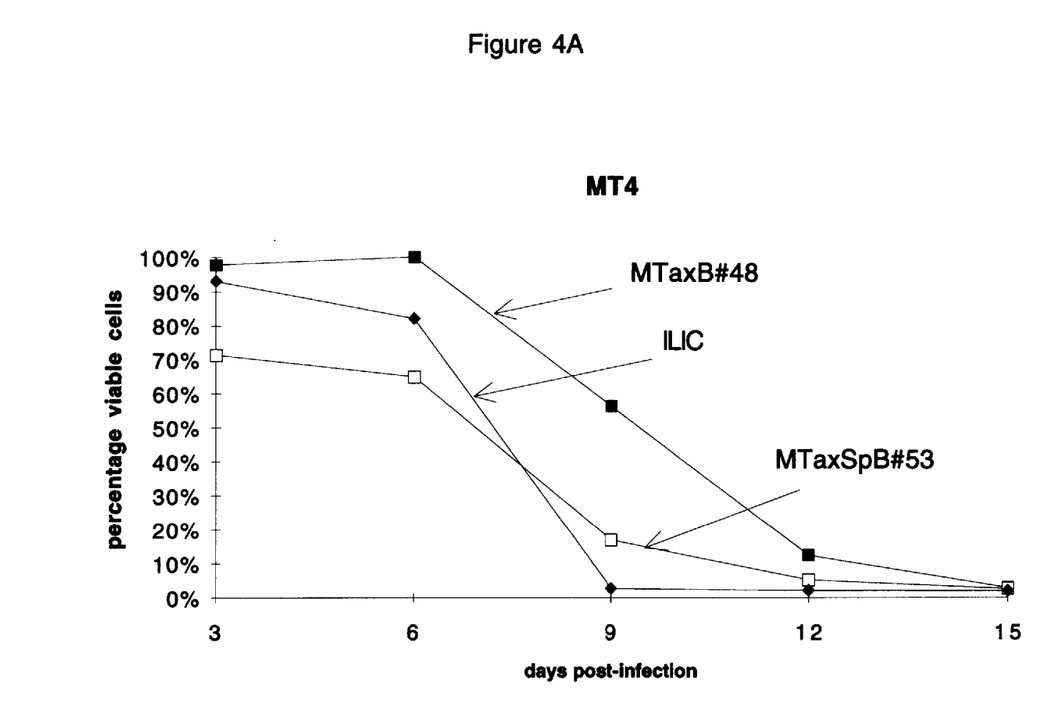
Figure 4B:
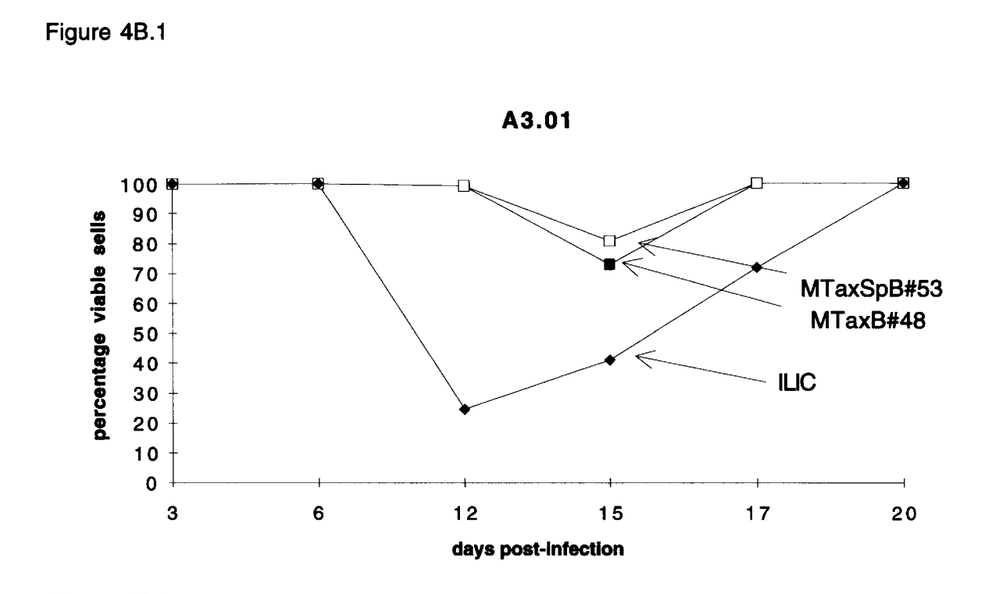
Figure 4B:
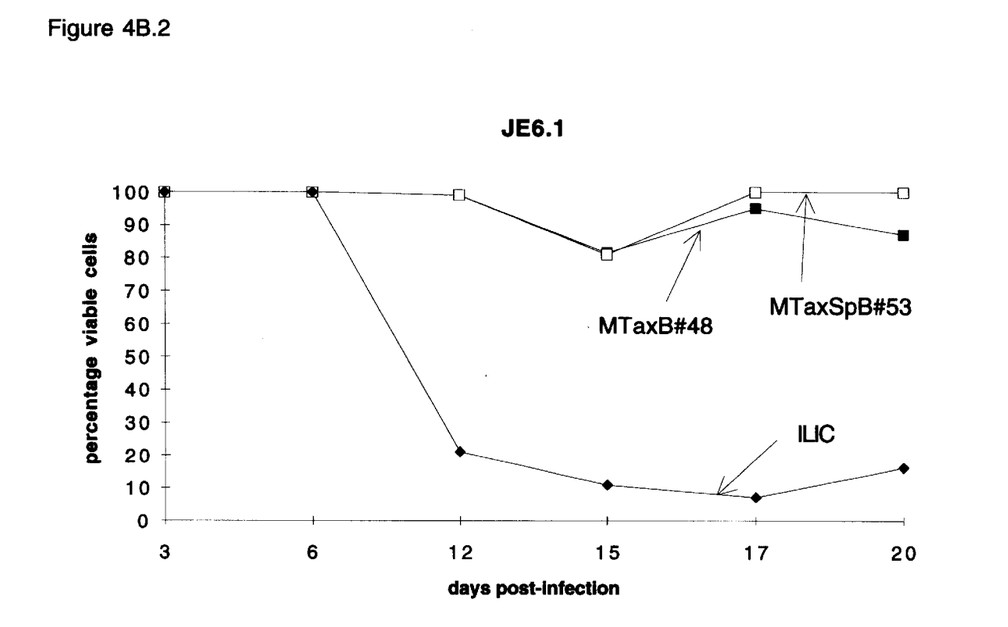

The selective replication of the TRE-viruses in HTLV-1 +cells is also associated with selective and specific cytotoxicity for these cells. As shown in FIG. 4A, infection of MT4 cells by either wild-type ILIC or the TRE-containing HIVs results in dramatic cell killing of the MT4 cells. In contrast, only the wildtype ILIC HIV exhibits marked cytotoxicity in the HTLV-1 negative Jurkat and A3.01 cell lines; no significant cell killing is observed with either of the TRE-containing HIVs studied (FIG. 4B). These results suggest that not only does insertion of the HTLV-1 TRE elements into the HIV LTR result in selective replication of these viruses into HTLV-1 +cells, these viruses also exhibit selective cell killing for these HTLV-1 Tax-expressing cells. These studies are the basis of the claim that insertion of the HTLV-1 TRE elements into the promoters of HIV or of HIV-derived vector systems may be used to selectively kill HTLV-1 tumor cells. Furthermore, as described below, these results provide the basis for the development of alternative gene therapy vectors based on murine leukemia virus-based gene delivery systems, that would express cytotoxic genes selectively in HTLV-1 + leukemic cells as a selective, cytocidal therapy for these tumors.

In summary, the data presented here demonstrate that replacement of the wild-type HIV promoter Sp1 and NF-kappa-B binding sites by the HTLV-1 21 bp Tax responsive element results in the generation of an HIV that specifically replicates in, and selectively kills HTLV-1 positive, Tax-expressing cells.

Throughout this application, various publications have been referenced. The disclosures in these publications are incorporated herein by reference in order to more fully describe the state of the art.

The invention being thus described, it will be obvious that the same may be varied in many ways. Such variations are not to be regarded as a departure from the spirit and scope of the invention and all such modifications are intended to be included within the scope of the following claims.

We claim:

1. An isolated human immunodeficiency virus type 1 (HIV-1) vector altered by having the HIV-1 long terminal repeat (LTR) promoter and enhancer sequences replaced by two copies of the HTLV-I LTR 21 base pair repeat Tax-responsive element (TRE), wherein the promoter and enhancer sequences consist of the NF-K-B and SP1 binding sites, and the altered HIV-1 vector will replicate only in human CD4+ cells that express the Tax protein of HTLV-I.

2. The isolated human immunodeficiency virus type 1 (HIV-1) vector of claim 1, wherein the vector further comprises a gene encoding a cytotoxic protein.

3. A method for killing HTLV-I infected cells ex vivo, which method comprises administering the altered HIV-1 vector of claim 1 to the cells, whereby the altered HIV-1 infects and replicates only in cells which are infected with HTLV-I and express the HTLV-1 Tax protein, thereby killing the HTLV-I infected cells.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 4 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:1:

G C G C        4

( 2 ) INFORMATION FOR SEQ ID NO:2:

( i ) SEQUENCE CHARACTERISTICS:
        ( A ) LENGTH: 8 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:2:

G C G C G C G C        8

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:3:

G C G C G C G C G C  G C G C G C        1 6

( 2 ) INFORMATION FOR SEQ ID NO:4:

( i ) SEQUENCE CHARACTERISTICS:
           ( A ) LENGTH: 72 base pairs
           ( B ) TYPE: nucleic acid
           ( C ) STRANDEDNESS: unknown
           ( D ) TOPOLOGY: unknown      ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:4:

```
TACAAGGGAC   TTTCCGCTGG   GGACTTTCCA   GGGAGGCGTG   GCCTGGGCGG   GACTGGGGAG        60

TGGCGAGCCC   TC                                                                   72
```

( 2 ) INFORMATION FOR SEQ ID NO:5:

( i ) SEQUENCE CHARACTERISTICS:
           ( A ) LENGTH: 10 base pairs
           ( B ) TYPE: nucleic acid
           ( C ) STRANDEDNESS: unknown
           ( D ) TOPOLOGY: unknown      ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:5:

```
TACAACGCGT                                                                        10
```

( 2 ) INFORMATION FOR SEQ ID NO:6:

( i ) SEQUENCE CHARACTERISTICS:
           ( A ) LENGTH: 8 base pairs
           ( B ) TYPE: nucleic acid
           ( C ) STRANDEDNESS: unknown
           ( D ) TOPOLOGY: unknown      ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:6:

```
GAGCCCTC                                                                           8
```

( 2 ) INFORMATION FOR SEQ ID NO:7:

( i ) SEQUENCE CHARACTERISTICS:
           ( A ) LENGTH: 120 base pairs
           ( B ) TYPE: nucleic acid
           ( C ) STRANDEDNESS: unknown
           ( D ) TOPOLOGY: unknown      ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:7:

```
ACGCGTCAGG   CGTTCACGAC   AACCCCTGCG   CGTCAGGCGT   TGACGACAAC   CCCTGCGCGT        60

CAGGCGTTGA   CGACAACCCC   TGCGCGTCTG   GGGCGGGAGC   GCGTCTGGGC   GGGAGCGCGT       120
```

( 2 ) INFORMATION FOR SEQ ID NO:8:

( i ) SEQUENCE CHARACTERISTICS:
        ( A ) LENGTH: 63 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:8:

```
TACAACGCGC  AGGGGTTGTC  CTAACGCCTG  ACGCGCAGGG  GTTGTCGTCA  ACGCCTGACG        60
CGT                                                                           63
```